(12) United States Patent
Bonrath et al.

(10) Patent No.: US 9,283,549 B2
(45) Date of Patent: Mar. 15, 2016

(54) METAL POWDERDOUS CATALYST COMPRISING A COCRMO-ALLOY

(71) Applicant: DSM IP ASSETS B.V., Heerlen (NL)

(72) Inventors: Werner Bonrath, Basel (CH); Axel Buss, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/380,195

(22) PCT Filed: Feb. 22, 2013

(86) PCT No.: PCT/EP2013/053511
§ 371 (c)(1),
(2) Date: Aug. 21, 2014

(87) PCT Pub. No.: WO2013/124391
PCT Pub. Date: Aug. 29, 2013

(65) Prior Publication Data
US 2015/0018585 A1   Jan. 15, 2015

(30) Foreign Application Priority Data
Feb. 24, 2012  (EP) .................................... 12156805

(51) Int. Cl.
| | |
|---|---|
| *B01J 23/26* | (2006.01) |
| *B01J 23/28* | (2006.01) |
| *B01J 23/56* | (2006.01) |
| *B01J 23/89* | (2006.01) |
| *B01J 37/02* | (2006.01) |
| *B01J 23/60* | (2006.01) |
| *B01J 35/00* | (2006.01) |
| *C07C 29/17* | (2006.01) |

(52) U.S. Cl.
CPC ............. *B01J 23/8993* (2013.01); *B01J 23/60* (2013.01); *B01J 35/006* (2013.01); *B01J 37/0207* (2013.01); *B01J 37/0225* (2013.01); *B01J 37/0226* (2013.01); *C07C 29/17* (2013.01)

(58) Field of Classification Search
CPC ............. B01J 23/26; B01J 23/28; B01J 23/56
USPC .................................... 568/903; 502/319, 321
See application file for complete search history.

(56) References Cited

FOREIGN PATENT DOCUMENTS

| WO | WO 2008/101603 | 8/2008 | | |
|---|---|---|---|---|
| WO | WO 2011/092280 | 8/2011 | | |
| WO | WO 2012/001166 | 1/2012 | | |
| WO | WO-2012/001166 | * | 1/2012 | ............. C07C 29/17 |

OTHER PUBLICATIONS

Semagina et al., "Structured Catalyst of PD/ZnO on Sintered Metal Fibers for 2-methyl-3-butyn-2-ol Selective Hydrogenation", Journal of Catalysis, vol. 251, No. 1, Sep. 7, 2007, pp. 213-222.

* cited by examiner

*Primary Examiner* — Kamal Saeed
*Assistant Examiner* — Janet L Coppins
(74) *Attorney, Agent, or Firm* — Nixon & Vanderhye P.C.

(57) ABSTRACT

The present invention is related to a new metal powder catalytic system (catalyst) comprising a cobalt/chrome-alloy as a carrier, its production and its use in hydrogenation processes.

17 Claims, No Drawings

METAL POWDERDOUS CATALYST COMPRISING A COCRMO-ALLOY

This application is the U.S. national phase of International Application No. PCT/EP2013/053511 filed 22 Feb. 2013 which designated the U.S. and claims priority to European Patent Application No. EP 12156805.9 filed 24 Feb. 2012, the entire contents of each of which are hereby incorporated by reference.

The present invention is related to a new metal powder catalytic system (catalyst) comprising a cobalt/chrome-alloy as a carrier, its production and its use in hydrogenation processes.

Powderous catalysts are well known and used in chemical reactions. Important types of such catalysts are i.e. the Lindlar catalysts.

A Lindlar catalyst is a heterogeneous catalyst which consists of palladium deposited on a calcium carbonate carrier which is also treated with various forms of lead.

Such catalysts are of such an importance that there is always a need for their improvement.

The goal of the present invention was to find a powderous catalyst with improved properties.

The powderous catalysts according to the present invention do have a metal (or metal alloy) as carrier material, instead of a calcium carbonate carrier.

This metal alloy is coated by a metal oxide layer on which palladium (Pd) is deposited.

Furthermore the new catalyst according to the present invention is free from lead (Pb).

The main components of the powderous metal alloy are cobalt (Co), chromium (Cr) and molybdenum (Mo).

Therefore, the present invention relates to a powderous catalytic system (I) comprising a metal alloy carrier comprising
  (i) 55 weight-% (wt-%)-80 wt-%, based on the total weight of the metal alloy, of Co, and
  (ii) 20 wt-%-40 wt-%, based on the total weight of the metal alloy, of Cr, and
  (iii) 2 wt-%-10 wt-%, based on the total weight of the metal alloy, of Mo, and
wherein the said metal alloy is coated by a metal oxide layer and impregnated with Pd.

It is obvious that all percentages always add up to 100.

The catalytic system is in the form of a powder.

This new catalyst has numerous advantages:

The catalyst is easy to recycle (and to remove) after the reaction. This can be done i.e. by filtration.

The catalyst can be used more than once (re-usable).

The catalyst as such is a very stable system. It is i.e. stable in regard to acids as well as to water.

The catalyst is easy to produce.

The catalyst is easy to handle.

The hydrogenation can be carried out without any solvents.

The catalyst is free from lead.

The catalyst shows high selectivity in hydrogenation reactions.

The metal alloys used as a carrier are known as cobalt/chromium/molybdenum alloy. Such alloys are available commercially, i.e. from EOS GmbH Germany (EOS CobaltChrome MP1®), from Attenborough Dental UK (Megallium®) and from International Nickel.

Such alloys are usually used in the field of dentistry. Especially, they are used in the production of dental prostheses.

Therefore it is surprising that such materials have excellent properties, when they are used as catalysts in hydrogenations.

Preferably, the present invention relates to a powderous catalytic system (II), wherein the metal alloy comprises
  (i) 55 wt-%-70 wt-%, based on the total weight of the metal alloy, of Co, and
  (ii) 20 wt-%-35 wt-%, based on the total weight of the metal alloy, of Cr, and
  (iii) 4 wt-%-10 wt-%, based on the total weight of the metal alloy, of Mo, and
wherein the said metal alloy is coated by a metal oxide layer impregnated with Pd.

The metal alloy can comprise further metals, such as i.e. Cu, Fe, Ni, Mn, Si, Ti, Al and/or Nb.

Therefore, the present invention also relates to a powderous catalytic system (III), which is a powderous catalytic system (I) and/or (II), wherein the alloy comprises further metals, such as i.e. Cu, Fe, Ni, Mn, Si, Ti, Al and/or Nb.

Furthermore the metal alloy can comprise carbon as well.

Therefore, the present invention also relates to a powderous catalytic system (IV), which is a powderous catalytic system (I), (II) and/or (III), wherein the alloy comprises carbon.

The metal oxide layer, which coats the metal alloy, is non-acidic (preferably basic or amphoteric). Suitable non-acidic metal oxide layers comprise Zn, Cr, Mn, Cu or Al. Preferably the oxide layer comprise ZnO and optionally at least one further metal oxide wherein the metal is chosen from the group consisting of Cr, Mn, Mg, Cu and Al.

Therefore the present invention also relates to a powderous catalytic system (V), wherein powderous catalytic system (I), (II), (III) and/or (IV) the metal oxide layer is non-acidic (preferably basic or amphoteric).

Preferred is a powderous catalytic system (V'), which is powderous catalytic system (V), wherein the non-acidic metal oxide layer comprises Zn, Cr, Mn, Cu and/or Al (more preferably the oxide layer comprise ZnO and optionally at least one further metal oxide wherein the metal is chosen from the group consisting of Cr, Mn, Mg, Cu and Al).

Preferred is also a powderous catalytic system (V"), which is powderous catalytic system (V') wherein the non-acidic metal oxide layer is essentially free from Pb.

The metal alloy is preferably coated with a thin layer of ZnO (0.5-3.5 µm thickness) and optionally at least one further metal (Cr, Mn, Mg, Cu and/or Al) oxide.

Therefore the present invention also relates to a powderous catalytic system (VI), which is powderous catalytic system (I), (II), (III), (IV), (V), (V') and/or (V"), wherein the metal alloy is coated with a thin layer of ZnO and optionally at least one further metal (Cr, Mn, Mg, Cu and/or Al) oxide.

The coating of the metal alloy is done by commonly known processes, such as i.e. dip-coating.

Usually the catalyst of the present invention comprises between 0.1 wt-% and 50 wt-%, based on the total weight of the catalyst, of ZnO, preferably between 0.1 wt-% and 30 wt-%, more preferably between 1.5 wt-% and 10 wt-% and most preferably between 2 wt-% and 8 wt-%.

Therefore the present invention also relates to a powderous catalytic system (VII), which is powderous catalytic system (I), (II), (III), (IV), (V), (V'), (V") and/or (VI), wherein the catalyst comprises between 0.1 wt-% and 50 wt-%, based on the total weight of the catalytic system, of ZnO (preferably between 0.1 wt-% and 30 wt-%, more preferably between 1.5 wt-% and 10 wt-% and most preferably between 2 wt-% and 8 wt-%).

In a preferred embodiment of the present invention the non-acidic metal oxide layers comprises ZnO and at least one further metal oxide wherein the metal is chosen from the group consisting of Cr, Mn, Mg, Cu and Al.

In a more preferred embodiment of the present the non-acidic metal oxide layer comprises ZnO and $Al_2O_3$.

Therefore the present invention also relates to a powderous catalytic system (VIII), which is powderous catalytic system (I), (II), (III), (IV), (V), (V'), (V"), (VI) and/or (VII), wherein the non-acidic metal oxide layer comprises ZnO and $Al_2O_3$.

When a mixture of ZnO and $Al_2O_3$ is used then it is preferred that the ratio of ZnO:$Al_2O_3$ is from 2:1 to 1:2 (preferably 1:1).

Therefore the present invention also relates to a powderous catalytic system (VIII'), which is powderous catalytic system (VIII), wherein the ratio of ZnO:$Al_2O_3$ is from 2:1 to 1:2 (preferably 1:1).

The coated metal alloys are then impregnated by Pd-nanoparticles. The nanoparticles are synthesized by commonly known methods, i.e. by using $PdCl_2$ as a precursor, which is then reduced by hydrogen.

Usually the Pd-nanoparticles, which are on the non-acidic metal oxide layer, have an average particle size of between 0.5 and 20 nm, preferably of between 2 and 15 nm, more preferably of between 5 and 12 nm and most preferably of between 7 to 10 nm. (The size is measured by light scattering methods).

Therefore the present invention also relates to a powderous catalytic system (IX), which is powderous catalytic system (I), (II), (III), (IV), (V), (V'), (V"), (VI), (VII), (VIII) and/or (VIII'), wherein the Pd-nanoparticles have an average particle size of between 0.5 and 20 nm (preferably of between 2 and 15 nm, more preferably of between 5 and 12 nm and most preferably of between 7 to 10 nm).

The catalyst according to present invention comprises between 0.001 wt-% and 5 wt-%, based on the total weight of the catalyst, of the Pd-nanoparticles, preferably between 0.01 wt-% and 2 wt-% more preferably between 0.05 wt-% and 1 wt-%.

Therefore the present invention also relates to a powderous catalytic system (X), which is powderous catalytic system (I), (II), (III), (IV), (V), (V'), (V"), (VI), (VII), (VIII), (VIII') and/or (IX), wherein the catalyst comprises between 0.001 wt-% and 5 wt-%, based on the total weight of the catalyst, of the Pd-nanoparticles (preferably between 0.01 wt-% and 2 wt-% more preferably between 0.05 wt-% and 1 wt-%).

The catalyst is usually activated before the use. The activation is done by using well known processes, such thermo activation in $H_2$.

The catalyst of the present invention is used in selective catalytic hydrogenation of organic starting material, especially of organic starting material comprising a carbon-carbon triple bond, more especially of alkynol compounds.

Therefore the present invention also relates to the use of a powderous catalytic system (catalyst) (I), (II), (III), (IV), (V), (V'), (V"), (VI), (VII), (VIII), (VIII'), (IX) and/or (X) in selective catalytic hydrogenation of organic starting material, especially of organic starting material comprising a carbon-carbon triple bond, more especially of alkynol compounds.

Preferably the present invention relates to a process of reacting a compound of formula (I)

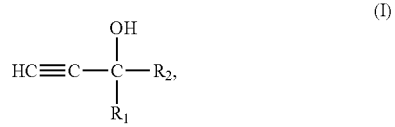

wherein $R_1$ is linear or branched $C_5$-$C_{35}$ alkyl; or linear or branched $C_5$-$C_{35}$ alkenyl moiety, wherein the C chain can be substituted, and $R_2$ is linear or branched $C_1$-$C_4$ alkyl, wherein the C chain can be substituted, with hydrogen in the presence of a catalyst (I), (II), (III), (IV) (V), (V'), (V"), (VI), (VII), (VIII), (VIII'), (IX) and/or (X).

Hydrogen is usually used in the form $H_2$ gas.

Preferred compounds of formula (I) are the following:

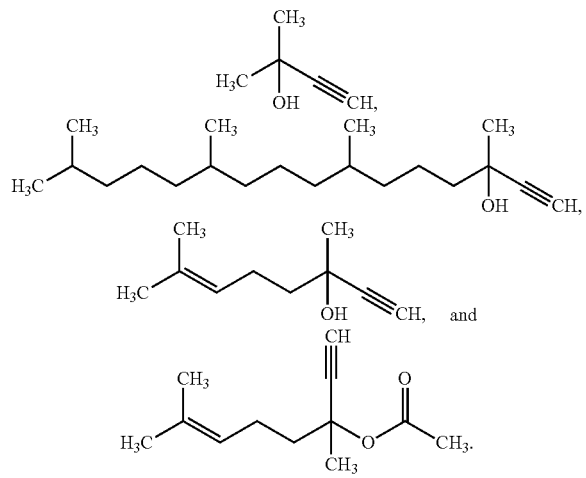

The following examples serve to illustrate the invention. All percentages are related to weight and the temperatures are given in degree Celsius, if not otherwise stated.

EXAMPLES

Example 1

Synthesis of the Catalyst
(Cobalt/Chromium/Molybdenum Alloy Coated by $Al_2O_3$/ZnO and Pd Deposition)

Step 1: Thermal Pre-Treatment

The metal alloy powder (EOS CobaltChrome MP1 ® commercially available from EOS GmbH, Germany) was subjected to a thermal pre-treatment at 450° C. for 3 h.

Step 2 Deposition of ZnO+$Al_2O_3$ (Coating of the Metal Alloy Carrier)

To a 100 ml-flask 20.0 g (53.3 mMol) of $Al(NO_3)_3 \cdot 9H_2O$ and 70 ml of water were added. The mixture was stirred until the $Al(NO_3)_3 \cdot 9H_2O$ was completely dissolved. The solution was heated up to 95° C. Then 4.34 g (53.3 mMol) of ZnO powder was slowly added to the reaction solution. Heating and stirring were maintained until the ZnO was completely dissolved. The solution was then cooled down to room temperature and filtrated through a membrane filter.

The deposition of ZnO/$Al_2O_3$ was performed by adding the oxidized metal alloy powder (10.0 g) from step 1 to the precursor solution and stirring the mixture at room temperature for 15 min.

The powder was then filtered off via a membrane filter and dried in air at 40° C. and 125 mbar for 2 h followed by a calcination step at 450° C. for 1 h. The stirring-drying-calcination cycle was repeated 3 times. Finally, the powder support was calcined in air at 550° C. for 1 h.

9.38 g of coated metal alloy powder was obtained.

Step 3: Preparation and Deposition of the Pd-Nanoparticles 318 mg (1.31 mmol) of sodium molybdate dihydrate and 212 mg (1.20 mmol) of palladium(II) chloride anhydrous were added to 60 ml of deionized water under heating (ca. 95° C.). The mixture was stirred. The heating and stirring were continued until complete evaporation of the water (solid residue was formed). Afterwards, 60 ml of deionized water were added to the residue under stirring. The evaporation-dissolving cycle was repeated two times in order to completely dissolve $PdCl_2$. Finally, 100 ml of hot water were added to the solid residue. The deep brown solution was cooled down to room temperature and filtrated through a paper filter. The filter was washed with water until the final volume of the precursor solution was 120 mL.

Afterwards the $Pd^o$ suspension was formed by bubbling hydrogen through the precursor solution for 1 h in a glass cylinder at room temperature.

The so obtained $Pd^o$ suspension and 9.38 g of the coated metal alloy powder (from step 2) were added to a 200 ml-flask. The mixture was stirred at room temperature for 15 min. The powder was filtered off via a filter paper and dried in air at 40° C. and 125 mbar for 2 h. This process was repeated twice.

Step 4: Thermo Activation of the Catalyst in $H_2$

The powder catalyst obtained from step 3 was subjected to a temperature treatment at 300° C. for 4 h under $H_2$—Ar flow. Then, it was cooled down to room temperature under the same $H_2$—Ar flow.

8.85 g of the powderous catalyst according to the present invention was obtained.

Example 2a

Selective Hydrogenation of MBY to MBE

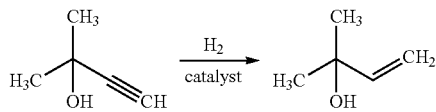

To 285 g (3.38 Mol) of MBY 1.5 g of the catalyst of Example 1 was added under stirring. The reaction was carried out at 65° C. and 4 bar pressure for about 7 hours.

At the end of the reaction the selectivity of the reaction was 96.42% and the conversion was 99.43%.

It can be seen that the new powderous catalyst has excellent properties as a catalyst for selective hydrogenations.

Example 2b

Repeated Selective Hydrogenation of MBY to MBE

The same reaction conditions as in Example 2a have been used. At the end of the reaction (after about 7-9 hours), the reaction mixture was cooled down under inter atmosphere and the reaction solution was exchanged with new MBY (again 285 g) and the hydrogenation was started again.

11 cycles have been run. The following table shows the results of the cycles.

| Cycles | Selectivity [%] | Conversion [%] | Yield [%] |
|---|---|---|---|
| 1 | 95.79 | 99.97 | 95.8 |
| 2 | 95.28 | 99.96 | 95.2 |
| 3 | 95.13 | 99.89 | 95.0 |
| 4 | 95.01 | 99.96 | 95.0 |
| 5 | 94.82 | 99.95 | 94.8 |
| 6 | 94.64 | 100.0 | 94.6 |
| 7 | 94.62 | 99.97 | 94.6 |
| 8 | 94.47 | 99.92 | 94.4 |
| 9 | 94.33 | 100.0 | 94.3 |
| 10 | 93.54 | 99.91 | 93.5 |
| 11 | 93.43 | 99.78 | 93.2 |

It can be seen that the new powderous catalyst keeps the excellent catalytic properties even after 11 cycles (without treating the catalyst).

Example 3a-3d

Selective Hydrogenation of Dehydroisophytol (DIP)

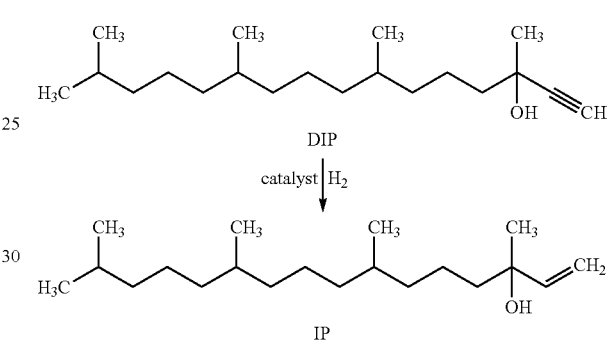

To 285 g (0.97 Mol) of DIP 1.5 g of the catalyst of Example 1 was added under stirring. The reaction was carried out at 85° C. and 4 bar pressure for about 4.5 hours.

At the end of the reaction the selectivity of the reaction was 81.76% and the conversion was 87.15%.

This example was repeated 3 times, wherein the following conversion and selectivity values resulted:

| Example | Conversion [%] | Selectivity [%] |
|---|---|---|
| 3b | 85.41 | 86.68 |
| 3c | 92.19 | 85.24 |
| 3d | 99.45 | 83.84 |

It can be seen that the new powderous catalyst has excellent properties as a catalyst for selective hydrogenations.

Example 3e-3i

Selective Hydrogenation of Dehydroisophytol (DIP) with a Basic Modifier

To 285 g (0.97 Mol) of DIP 1.5 g of the catalyst of Example 1 and a basic modifier (Tegochrome 22=2,2-Ethylene-dithiodiethanol) was added under stirring. The reaction was carried out at 85° C. and 4 bar pressure for about 7 hours.

At the end of the reaction the selectivity of the reaction was 82.02% and the conversion was 87.51%.

This example was repeated 4 times, wherein the following conversion and selectivity values resulted:

| Example | Conversion [%] | Selectivity [%] |
|---|---|---|
| 3f | 86.56 | 87.03 |
| 3g | 90.88 | 86.29 |
| 3h | 94.59 | 85.48 |
| 3i | 99.45 | 83.84 |

Example 3k

Repeated Selective of Dehydroisophytol (DIP) with a Basic Modifier

The same reaction conditions as in Examples 3e-3i have been used.

At the end of the reaction (after about 2.5-3 hours), the reaction mixture was cooled down under inter atmosphere and the reaction solution was exchanged with new DIP (again 285 g) and the hydrogenation was started again.

5 cycles have been run. The following table shows the results of the cycles.

| Cycles | Selectivity [%] | Conversion [%] | Yield [%] |
|---|---|---|---|
| 1 | 82.46 | 99.82 | 82.30 |
| 2 | 81.65 | 99.65 | 81.40 |
| 3 | 81.57 | 99.15 | 80.90 |
| 4 | 81.20 | 99.39 | 80.70 |
| 5 | 82.36 | 98.38 | 81.00 |

It can be seen that the new powderous catalyst keeps the excellent catalytic properties even after 5 cycles (without treating the catalyst).

Example 4

Selective Hydrogenation of Dehydrolinalool (DLL)

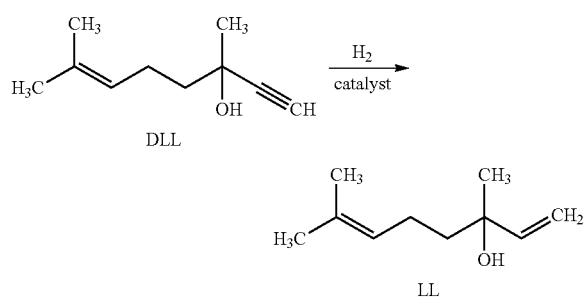

To 285 g (1.87 Mol) of DLL 1.5 g of the catalyst of Example 1 was added under stirring. The reaction was carried out at 55° C. and 4 bar pressure for about 6 hours.

At the end of the reaction the selectivity of the reaction was 92.08% and the conversion was 99.38%.

Example 5

Selective Hydrogenation of Dehydrolinalyl Acetate (DLA)

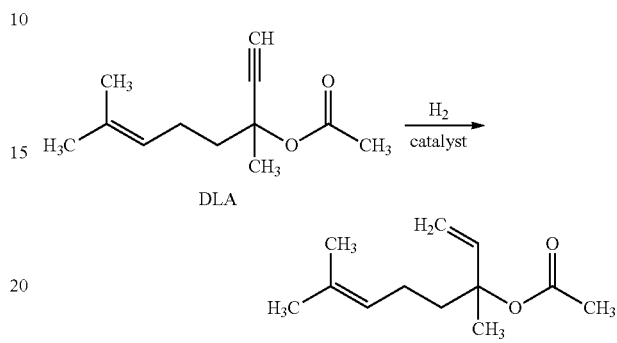

To 285 g (1.45 Mol) of DLA 1.5 g of the catalyst of Example 1 was added under stirring. The reaction was carried out at 40° C. and 4 bar pressure for about 7 hours.

At the end of the reaction the selectivity of the reaction was 88.22% and the conversion was 94.98%.

The invention claimed is:

1. A powderous catalytic system comprising powder particles formed of a metal alloy carrier which is coated by a metal oxide layer impregnated with Pd particles, wherein the metal alloy carrier comprises:
   (i) 55 wt-%-80 wt-%, based on the total weight of the metal alloy, of Co, and
   (ii) 20 wt-%-40 wt-%, based on the total weight of the metal alloy, of Cr, and
   (iii) 2 wt-%-10 wt-%, based on the total weight of the metal alloy, of Mo.

2. The powderous catalytic system according to claim 1, wherein the metal alloy carrier further comprises metals other than Co, Cr and Mo.

3. The powderous catalytic system according to claim 1, wherein the metal alloy carrier further comprises carbon.

4. The powderous catalytic system according to claim 1, wherein the metal alloy carrier comprises Co in an amount of 55 wt-%-70 wt-%, based on the total weight of the metal alloy carrier.

5. The powderous catalytic system according to claim 1, wherein the metal alloy comprises Cr in an amount of 20 wt-%-35 wt-%, based on the total weight of the metal alloy carrier.

6. Catalyst according to claim 1, wherein the metal alloy comprises 4 wt-%-10 wt-%, based on the total weight of the metal alloy, of Mo.

7. The powderous catalytic system according to claim 1, wherein the metal oxide layer is basic or amphoteric.

8. The powderous catalytic system according to claim 1, wherein the metal oxide layer comprises Zn, Cr, Mn, Cu and/or Al.

9. The powderous catalytic system according to claim 1, wherein the metal oxide layer comprises ZnO and optionally at least one further metal oxide selected from the group consisting of Cr, Mn, Mg, Cu and Al.

10. The powderous catalytic system according to claim 1, wherein the metal oxide layer comprises ZnO and $Al_2O_3$.

11. The powderous catalytic system according to claim 1, wherein the metal oxide layer is non-acidic, and wherein the non-acidic metal oxide layer is present in an amount between 0.1 wt-% and 50 wt-%, based on the total weight of the catalytic system.

12. The powderous catalytic system according to claim 1, wherein the metal oxide layer is a mixture of ZnO and $Al_2O_3$ in a ratio of ZnO to $Al_2O_3$ of from 2:1 to 1:2.

13. The powderous catalytic system according to claim 1, wherein the Pd particles are nanoparticles having an average particle size of between 0.5 and 20 nm.

14. The powderous catalytic system according to claim 13, wherein the Pd nanoparticles are present in an amount between 0.001 wt-% and 5 wt-%, based on the total weight of the catalytic system.

15. The powderous catalytic system according to claim 12, wherein the ratio of ZnO to $Al_2O_3$ in the metal oxide layer is 1:1.

16. A method for the selective hydrogenation of an organic starting material which comprises bringing the organic starting material into contact with the powderous catalytic system according to claim 1 under selective hydrogenation conditions.

17. The method according to claim 16, wherein the organic starting material is a compound of formula (I)

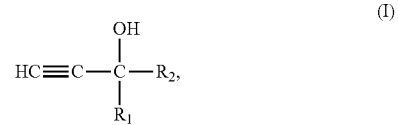

wherein
$R_1$ is linear or branched $C_5$-$C_{35}$ alkyl or linear or branched $C_5$-$C_{35}$ alkenyl moiety, wherein the C chain can be substituted, and
$R_2$ is linear or branched $C_1$-$C_4$ alkyl, wherein the C chain can be substituted.

* * * * *